United States Patent
Raybuck et al.

(10) Patent No.: US 7,551,077 B2
(45) Date of Patent: Jun. 23, 2009

(54) RFID RING ILLUMINATION SYSTEM FOR SURGICAL MACHINE

(75) Inventors: John L. Raybuck, Irvine, CA (US); Ronald T. Smith, Newport Coast, CA (US)

(73) Assignee: Alcon, Inc., Hunenberg (CH)

( * ) Notice: Subject to any disclaimer, the term of this patent is extended or adjusted under 35 U.S.C. 154(b) by 374 days.

(21) Appl. No.: 11/496,228

(22) Filed: Jul. 31, 2006

(65) Prior Publication Data

US 2008/0030343 A1 Feb. 7, 2008

(51) Int. Cl.
*G08B 1/08* (2006.01)

(52) U.S. Cl. .............. 340/539.12; 340/539.26; 340/572.1; 340/572.4; 340/572.8; 600/300; 600/301; 606/169; 606/170; 606/171; 200/314; 200/341; 200/520

(58) Field of Classification Search ............ 340/539.12, 340/572.1, 572.4, 572.8, 539.26, 572.6; 600/300, 301; 606/169, 170, 171; 200/314, 200/341, 520

See application file for complete search history.

(56) References Cited

U.S. PATENT DOCUMENTS

| | | | |
|---|---|---|---|
| 4,623,776 A | 11/1986 | Buchroeder et al. | |
| 4,749,832 A * | 6/1988 | Schlosser | 200/314 |
| 5,052,725 A | 10/1991 | Meyer et al. | |
| 5,085,492 A | 2/1992 | Kelsoe et al. | |
| 5,104,158 A | 4/1992 | Meyer et al. | |
| 5,400,267 A | 3/1995 | Denen et al. | |
| 5,475,571 A | 12/1995 | Dassanayake | |
| 5,494,074 A | 2/1996 | Ramacier, Jr. et al. | |
| 5,861,636 A * | 1/1999 | Dutta et al. | 257/91 |
| 5,911,403 A | 6/1999 | deCler et al. | |
| 5,975,489 A | 11/1999 | deCler et al. | |
| 5,975,711 A | 11/1999 | Parker et al. | |
| 6,024,124 A | 2/2000 | Braun et al. | |
| 6,082,401 A | 7/2000 | Braun et al. | |
| 6,161,578 A | 12/2000 | Braun et al. | |
| 6,172,609 B1 | 1/2001 | Lu et al. | |
| 6,231,089 B1 | 5/2001 | deCler et al. | |
| 6,273,338 B1 | 8/2001 | White | |
| 6,382,593 B1 | 5/2002 | deCler et al. | |

(Continued)

FOREIGN PATENT DOCUMENTS

EP 1 199 046 A2 4/2002

(Continued)

OTHER PUBLICATIONS

Appleby, "Drug makers using spy-novel strategies to thwart knockoffs," The Seattle Times, Aug. 19, 2003.

(Continued)

*Primary Examiner*—Tai T Nguyen
(74) *Attorney, Agent, or Firm*—Kenneth D. Bassinger

(57) ABSTRACT

An RFID ring illumination system includes an illumination ring and a printed circuit board. The illumination ring has a light refracting layer integral with the front of a surgical machine. The printed circuit board is located behind and close to the front of the surgical machine. The printed circuit board has an RFID reader antenna and a light source mounted on it. The light emitted by the light source travels through the illumination ring and is visible from the front of the surgical machine.

17 Claims, 11 Drawing Sheets

U.S. PATENT DOCUMENTS

| | | |
|---|---|---|
| 6,430,371 B1 | 8/2002 | Cho |
| 6,574,166 B2 | 6/2003 | Niemiec |
| 6,626,419 B2 | 9/2003 | deCler et al. |
| 6,649,829 B2 | 11/2003 | Garber et al. |
| 6,705,591 B2 | 3/2004 | deCler et al. |
| 6,747,226 B2 * | 6/2004 | Watanabe .................. 200/520 |
| 6,848,602 B2 | 2/2005 | deCler et al. |
| 6,861,954 B2 | 3/2005 | Levin |
| 6,897,374 B2 | 5/2005 | Garber et al. |
| 6,899,476 B1 | 5/2005 | Barrus et al. |
| 6,902,144 B2 | 6/2005 | deCler et al. |
| 6,903,656 B1 | 6/2005 | Lee |
| 6,916,007 B2 | 7/2005 | deCler et al. |
| 6,917,291 B2 | 7/2005 | Allen |
| 6,978,800 B2 | 12/2005 | deCler et al. |
| 7,038,398 B1 | 5/2006 | Lys et al. |
| 2001/0020148 A1 | 9/2001 | Sasse et al. |
| 2002/0017996 A1 | 2/2002 | Niemiec |
| 2002/0032435 A1 | 3/2002 | Levin |
| 2002/0143320 A1 | 10/2002 | Levin |
| 2003/0127508 A1 | 7/2003 | Jones |
| 2003/0178488 A1 | 9/2003 | Southard |
| 2003/0178489 A1 | 9/2003 | Boukhny et al. |
| 2004/0220602 A1 | 11/2004 | Deng et al. |
| 2004/0257007 A1 | 12/2004 | Lys et al. |
| 2005/0171408 A1 | 8/2005 | Parker et al. |
| 2006/0119481 A1 | 6/2006 | Tethrake et al. |
| 2006/0129140 A1 * | 6/2006 | Todd et al. .................... 606/1 |

FOREIGN PATENT DOCUMENTS

| | | |
|---|---|---|
| KR | 20010082793 A | 8/2001 |
| WO | WO 01/14912 A1 | 3/2001 |
| WO | WO 02/099774 A2 | 12/2002 |
| WO | WO 03/026558 A2 | 4/2003 |
| WO | WO 2006/036600 A1 | 4/2006 |

OTHER PUBLICATIONS

Baschet-Vernet, "Smart packages may help control prescriptions," Pharmpack Europe, Nov. 2002(5).

Atmel Corporation, "Electronic Immobilizers for the Automotive Industry," U2270B, Rev. 2661A-RFID Jun. 2003.

Lee, Dr. Youbok, "MCRF, 355/360 Applications," Microchip Technology, Inc., AN707, 1999:DS00707A, p. 1.

* cited by examiner

RFID RING ILLUMINATION SYSTEM FOR SURGICAL MACHINE

FIELD OF THE INVENTION

The present invention relates to surgical machines and more particularly to an RFID and ring illumination system for facilitating the connection of accessories to a surgical machine.

BACKGROUND OF THE INVENTION

Many operations performed today involve the use of complex surgical machines. Computerized equipment is often used by surgeons in the operating room (OR) to conduct surgery. These machines monitor and implement various stages of an operation. For example, in ophthalmic surgery, computerized machines and associated tools are used by a surgeon to perform cataract removal and lens replacement. Other machines are used to perform retinal surgery. These machines allow the surgeon to proceed through the steps of an operation.

Most surgical machines are designed to work with various tools. In ophthalmic surgery, these tools include probes, scissors, hand pieces, illuminators, lasers, and consumables. These tools are designed to connect to the front console of the surgical machine. For example, a surgeon performing retinal surgery may attach a small pair of pneumatically driven scissors to the machine. The scissors, in the form of a hand piece, are connected to a pneumatic connector on the front console of the machine with a cable. The cable provides the pneumatic power required to operate the scissors. One end of the cable is attached to the scissors while the other end has a connector designed to couple with the pneumatic connector on the front console of the machine.

Typically, the front console of the machine has a number of connectors designed to connect with and power various tools. For example, one connector may be designed to provide pneumatic power to a tool while another connecter may be designed to provide electric power to a different tool. In addition, a single pneumatic connector on the front console may be designed to interface with a number of different pneumatically-driven tools. Each tool that is plugged into the pneumatic connector will perform its intended function. One tool may be a pair of scissors used to cut tissue. Another tool may be a type of probe or a drug delivery device. Since each of these tools is designed to connect with the pneumatic connector on the console of the surgical machine, each is driven by the pneumatic power supplied by the machine.

A problem can arise during surgery when the wrong tool is connected to the machine. In such a case, the tool operates normally, but the wrong procedure is performed on the patient. For example, a surgeon may mistakenly attach a pair of pneumatically-driven scissors to a machine when he intends to attach a pneumatically-driven drug delivery device. The scissors will perform their intended function of cutting tissue. Since the surgeon intended to deliver a dosage of a drug, however, the unwanted cutting performed by the scissors can injure the patient.

As another example, there may be two different types of cutting tools. Each one may interface with the same connector on the front console of the machine. Using the wrong cutting tool can inflict unintended harm on the patient. Further, there may be two different types of electrically-driven tools, such as an illuminator and a laser. Using a laser when an illuminator is required can harm the patient. In sum, error on the part of the surgeon in using the wrong tool or the wrong type of tool can unintentionally injure a patient during an operation.

Further confusion can occur because of the labeling present on the front of a surgical machine. In conventional surgical machines, the connectors on the front console are passively labeled. A pneumatic connecter designed to work with several different tools may be labeled with a single icon, symbol or LED. This passive labeling may identify the type of connector or that power is being delivered through the connector, but such labeling is ineffective at preventing surgeon error.

In order to address this problem, some conventional surgical machines employ a set of different connectors for a set of different tools. In this manner, each tool is designed to mate with its own connector. However, this configuration of numerous different connectors can be confusing to the surgeon and adds additional expense and complexity to the design of the surgical machine. Moreover, different versions of the same type of tool may interface with a single one of the connectors on the front console of the machine. For example, two different types of scissors may be adapted to fit the same pneumatic connector on the front console of the machine. Using the wrong type of scissors might harm the patient.

Machines with conventional connectors also do not allow the collection of data from the tool. Since the physical connector on the front of the machine is often dumb, it cannot tell which tool is connected to it. Conventional connectors are adapted simply to provide the correct electric or pneumatic power to a tool. These connectors cannot discern what type of tool is connected to them. They also cannot identify a particular tool, how many times a particular tool was used, and other information about how the tool is operating or even if it is operating properly.

A smart connector system for a surgical machine is needed to address these problems. Patent application Ser. No. 11/491,068 filed Jul. 21, 2006, co-owned by applicant, describes such a system. In developing this system, it was discovered that a particular RFID illumination ring configuration overcomes additional problems.

An RFID system consists of two basic parts: an RFID reader and an RFID tag. The RFID reader typically includes a reader antenna, a transceiver, a microprocessor, a power supply, and signal conditioning circuitry. The RFID tag typically includes a tag antenna and an RFID label integrated circuit (IC). An RFID system allows data from the tag to be read by the RFID reader. In a typical RFID system, individual objects are equipped with a small, inexpensive tag. The tag contains an IC with memory to store information. This information is typically a unique code or some other other identifier. The RFID reader emits a signal activating the RFID tag so it can read and write data to it. When an RFID tag passes through the electromagnetic field emitted by the RFID reader, it detects the reader's activation signal. The reader then decodes the data encoded in the RFID tag's IC.

In one type of RFID system, a passive RFID system, the RFID tag does not have an internal power supply. Instead, the passive RFID tag relies on the electromagnetic field produced by the RFID reader for its power. The electromagnetic field produced by the RFID reader induces an small electrical current in the tag antenna. This small electrical current allows the tag IC to operate. In this passive system, the tag antenna is designed to both collect power from the electromagnetic field of the reader and to transmit an outbound signal. Passive tags have practical read distances ranging from about 2 mm up to a few meters depending on the chosen radio frequency and the size and shape of the antenna.

Semi-passive and active RFID tags have their own source of power. A semi-passive RFID tag typically uses a small battery for its power supply. Active RFID tags typically have an on-board power supply. The power provided by these sources allows a tag to perform additional functions.

Regardless of which type of RFID system is chosen, the closer the tag antenna is to the reader antenna, the better the system performs. Since the strength of an electromagnetic field emitted from an antenna decreases in proportion to the square of the distance from the antenna, it is desirable to have the tag antenna close to the reader antenna.

The reader antenna typically resides on a printed circuit board (PCB). To improve performance of the RFID system, it is desirable to place the PCB with the reader antenna close to the tag antenna. The tag antenna, however, is located on an item that is separate from and movable with respect to the PCB with the reader antenna. In the context of a surgical machine, the PCB with the reader antenna resides in the main console while the tag IC and tag antenna reside on a peripheral, such as a tool, that can be connected to the console of the surgical machine. It would be desirable to locate the PCB with the reader antenna close to the front panel of the surgical machine in a location close to where the tool attaches. The tag antenna can be located on the mating connector of the tool. When the mating connector of the tool is plugged into the connector on the front panel of the machine, the reader antenna and the tag antenna can be located very close to each other.

In a surgical machine with an illumination ring system, it would be desirable to locate the light emitting diodes (LEDs) that provide the light for the illumination ring on the same PCB that has the reader antenna. Having a single PCB for both the RFID reader and ring illumination functions reduces the number of parts needed to build the machine.

Traditionally, an illumination ring is a separate component implemented using a light pipe. A typical light pipe has multiple parts that complicate assembly during the manufacturing process. A light pipe also requires custom tooling. A light pipe can also be too long to fit in tight places, such as the space between the manifold and the front panel on a surgical machine. Another alternative that is traditionally employed is a light diffusing ring assembly. A light diffusing ring assembly also consists of separate parts that complicate assembly during the manufacturing process, requires more power, and utilizes relatively expensive LEDs.

It would be desirable to have an illumination ring incorporated into the front panel of a surgical machine with LEDs located on a PCB. Incorporating the illumination ring into the front panel would decrease the complexity of assembly during the manufacturing process and provide a smooth front panel surface that is less likely to trap dirt and germs. The fewer seams on the front panel of a surgical machine, the better for reducing the possiblility of contamination in an operating room. Since the surgical machine is located in an operating room, it is desirable to keep it clean to reduce the risk of infection. In addition, it would be desirable to have the RFID reader antenna on the same PCB that carries the LEDs. Having both the RFID reader antenna and the LEDs to light the illumination ring on the same PCB decreases the number of components needed and decreases the complexity of assembling a surgical machine.

SUMMARY OF THE INVENTION

In one embodiment consistent with the principles of the present invention, the present invention is a ring illumination system having an illumination ring and a printed circuit board. The illumination ring has a light refracting layer integral with the front of a surgical machine. The printed circuit board is located behind and close to the front of the surgical machine. The printed circuit board has an RFID reader antenna and a light source mounted on it. The light emitted by the light source travels through the illumination ring and is visible from the front of the surgical machine.

In another embodiment consistent with the principles of the present invention, the present invention is a ring illumination system having a module, an illumination ring, and a printed circuit board. The module has a front face and a back face. The illumination ring is integral with the module and extends from the front face of the module to the back face of the module. The printed circuit board is located behind and close to the back face of the module. The printed circuit board has an RFID reader antenna and a light source. The light emitted by the light source travels through the illumination ring and is visible from the front face of the module.

In another embodiment consistent with the principles of the present invention, the present invention is a ring illumination system having a light diffusing layer, a light refracting layer, and a printed circuit board. Both the light diffusing layer and the light refracting layer are integral with the front cover of the surgical machine. The light refracting layer has a set of prisms arranged in a generally circular pattern. The printed circuit board is located behind, close to, and generally parallel with the front cover of the surgical machine. The printed circuit board has an RFID reader antenna located on a face of the printed circuit board closest to the front cover of the surgical machine. The printed circuit board also has a set of light emitting diodes located on a face of the printed circuit board furthest from the front cover of the surgical machine. The printed circuit board further has a set of openings to allow light from the light emitting diodes to reach the light refracting layer. The light from the light emitting diodes is refracted by the light refracting layer and is diffused by the light diffusing layer to form a generally circular ring of light visible from the front cover of the surgical machine.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
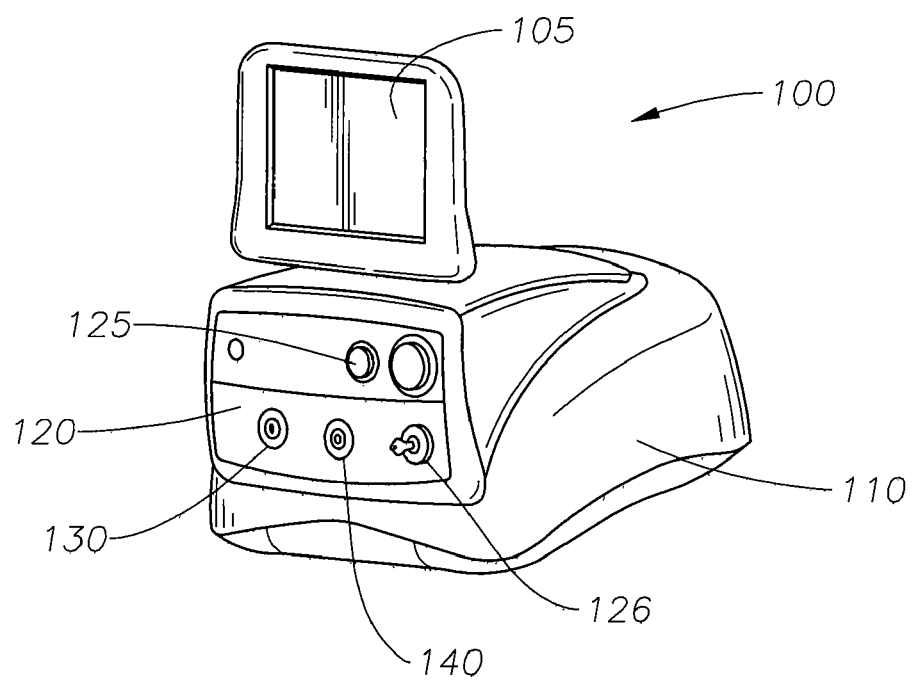
FIG. 1 is a perspective view of a surgical machine with an RFID illumination ring system according to an embodiment of the present invention.

FIG. 1 is a perspective view of a surgical machine 100 with an RFID illumination ring system according to an embodiment of the present invention. In FIG. 1, surgical machine 100 has a display 105 and a main surgical console 110. Information about the operation and status of surgical machine 100 is displayed on display 105. Main surgical console 110 contains the circuitry (not shown) to operate surgical machine 100. Main surgical console has a front panel 120 located on the front of surgical machine 100. Various controls, such as control knob 125 and key lock 126, are located on front panel 120. In addition, an electrical connector and illumination ring 130 and a pneumatic connector and illumination ring 140 are located on front panel 120. While the location of the controls 125,126 and the connectors and illumination rings 130,140 are shown on front panel 120, their location can be anywhere on main surgical console 110, display 105, or other peripheral (not shown). Surgical machine 100 also contains an RFID reader (not shown). A typical RFID reader includes an RFID antenna, transceiver, microprocessor, power supply, and signal conditioning circuitry.

Figure 2:
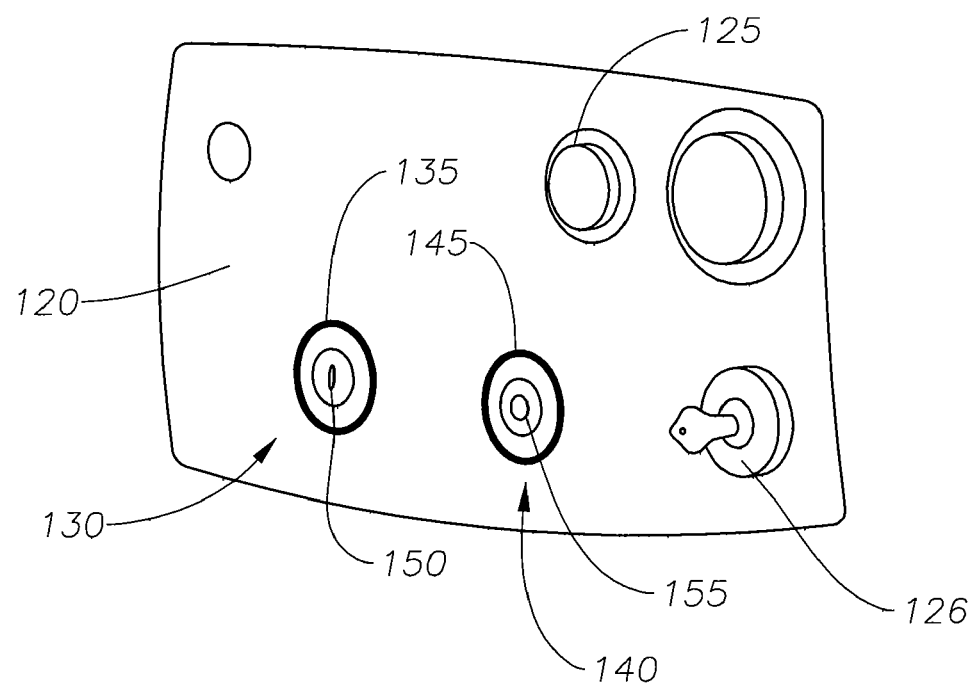
FIG. 2 is a perspective view of a front panel of a surgical machine with an RFID illumination ring system according to an embodiment of the present invention.

FIG. 2 shows a more detailed view of the front panel 120 depicted in FIG. 1. Front panel 120 holds controls, such as control knob 125 and key lock 126. Front panel 120 also has two connectors with illumination rings 130,140. Electrical connector with illumination ring 130 has an illumination ring 135 and an electrical connector 150. Illumination ring 135 is located around the periphery of electrical connector 150. Pneumatic connector with illumination ring 140 has an illumination ring 145 and a pneumatic connector 155. Illumination ring 145 is located around the periphery of pneumatic connector 155.

Electrical connector 150 is adapted to receive a mating connector from an electrically-powered accessory, such as a tool. When connected to an electrically-powered accessory, electrical connector 150 provides power to that accessory. Likewise, pneumatic connector 155 is adapted to receive a mating connector from a pneumatically-powered accessory, such as a tool. When connected to a pneumatically-powered accessory, pneumatic connector 155 provides power to that accessory.

The illumination rings 135, 145 are designed to display visible light in a ring-like configuration. In this manner, a surgeon operating the surgical machine 100 can see when an illumination ring is lit. Illumination rings 135, 145 are designed to display different colors indicating different modes of operation or statuses of the surgical machine 100 as discussed in further detail below. While shown as a continuous ring, illumination rings 135, 145 may take on numerous different configurations without departing from the scope and spirit of this invention. For example, illumination rings 135, 145 may be in the shape of a square, triangle, or any other polygon. In addition, the light produced by illumination rings 135, 145 need not be continuous as shown. While a continuous ring of light is generally more useful and aesthetically pleasing, a broken ring of light can also be used as can flashing or pulsating light.

Figure 3:
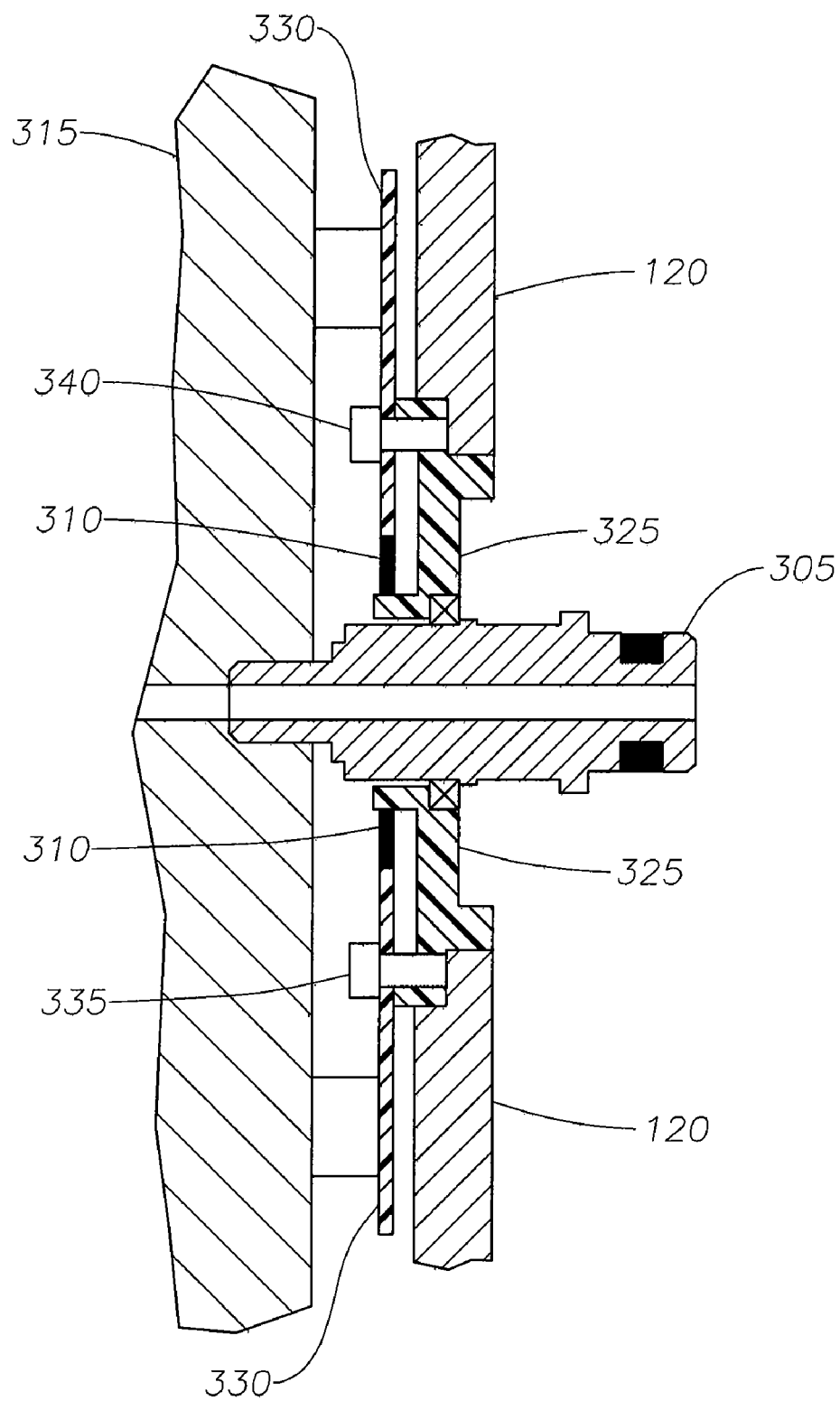
FIG. 3 is an exploded view of a connector and illumination ring on the front panel of a surgical machine with an RFID illumination ring system according to an embodiment of the present invention.

FIG. 3 is an exploded side view of a connector and illumination ring located on front panel 120 of surgical machine 100. In FIG. 3, male connector 305 is mounted onto manifold 315 of surgical machine 100. Manifold 315 is located behind and attached to front panel 120 of surgical machine 100. Printed circuit board (PCB) 330 is located between manifold 315 and front panel 120. Male connector protrudes through PCB 330 and front panel 120 to allow connection with a female connector on a tool (not shown). Light emitting diodes (LEDs) 335 and 340 are mounted on the side of PCB 330 that faces the manifold 315. In other words, LEDs 335 and 340 are mounted on the side of PCB 330 that does not face front panel 120. RFID reader antenna 310 is also located on or integrated into PCB 330. Lens 325 is located in front of PCB 330 and in a plane substantially parallel with front panel 120. The front face of lens 325 is visible when looking at the front panel 120.

In FIG. 3, an illumination ring is implemented with LEDs 335, 340 and lens 325. Light from LEDs 335, 340 passes through holes in the PCB 330 (not shown) and is refracted and diffused by lens 325. A ring of visible light is observed when looking at the lens 325 on front panel 120. In order to produce a uniform ring of light, lens 325 refracts and diffuses the light produced by LEDs 335, 340. In this manner, an illumination ring is located around the periphery of male connector 305.

Figure 4:
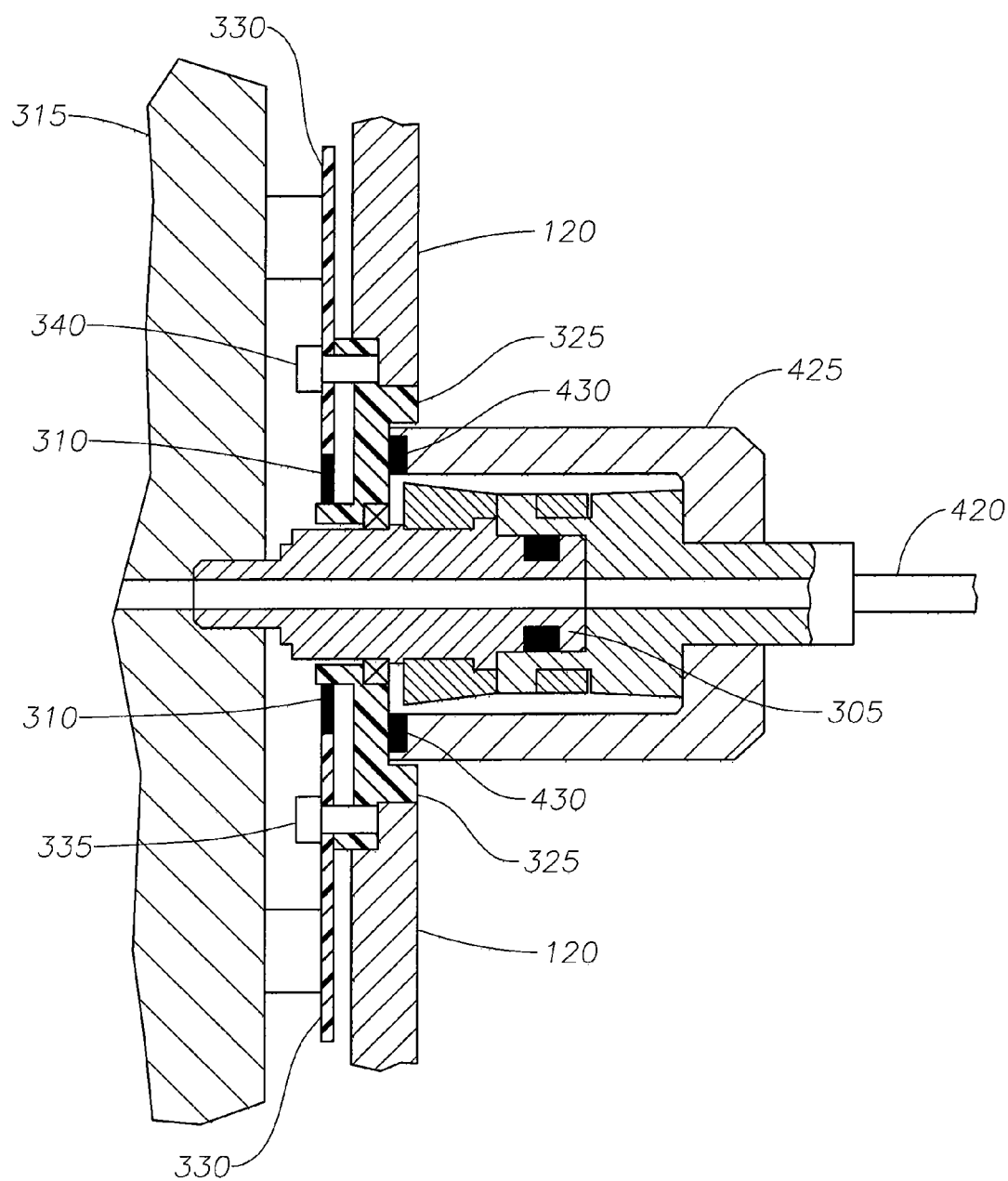
FIG. 4 is an exploded cross-section view of a connector and illumination ring on the front panel of a surgical machine with an RFID illumination ring system as coupled to a connector on a tool for use with a surgical machine with an RFID illumination ring system according to an embodiment of the present invention.

FIG. 4 is an exploded cross-section view of male connector and illumination ring on the front panel of a surgical machine as coupled to a connector on a tool. In FIG. 4, male connector 305 is mounted in manifold 315 of surgical machine 100. Manifold 315 is located behind and attached to front panel 120 of surgical machine 100. Printed circuit board (PCB) 330 is located between manifold 315 and front panel 120. Male connector protrudes through PCB 330 and front panel 120 to allow connection with a female connector on a tool Light emitting diodes (LEDs) 335 and 340 are mounted on the side of PCB 330 that faces the manifold 315. In other words, LEDs 335 and 340 are mounted on the side of PCB 330 that does not face front panel 120. RFID reader antenna 310 is also located on or integrated into PCB 330. Lens 325 is located in front of PCB 330 and in a plane substantially parallel with front panel 120. The front face of lens 325 is visible when looking at the front panel 120.

Female connector 425 includes a cable 420 and an RFID tag 430. The cable 420 extends from the connector 425 and toward the hand piece (not shown). RFID tag 430 is located on a front face of female connector 425. As shown, female connector 425 is coupled to male connector 305. In this configuration, a tool is connected to the surgical machine.

When female connector 425 is connected to male connector 305, RFID tag 430 is located close to reader antenna 310. This allows reader antenna 310 and RFID tag 430 to easily communicate with each other. Reader antenna 310 emits an RF field (not shown). When female connector 425 with RFID tag 430 is brought within this field, communication is established between RFID tag 430 and reader antenna 310. It is not necessary that female connector 425 and male connector 305 actually be coupled together for communication to take place. It is only necessary that RFID tag 430 be brought into the RF field emitted from reader antenna 310.

Figure 5:
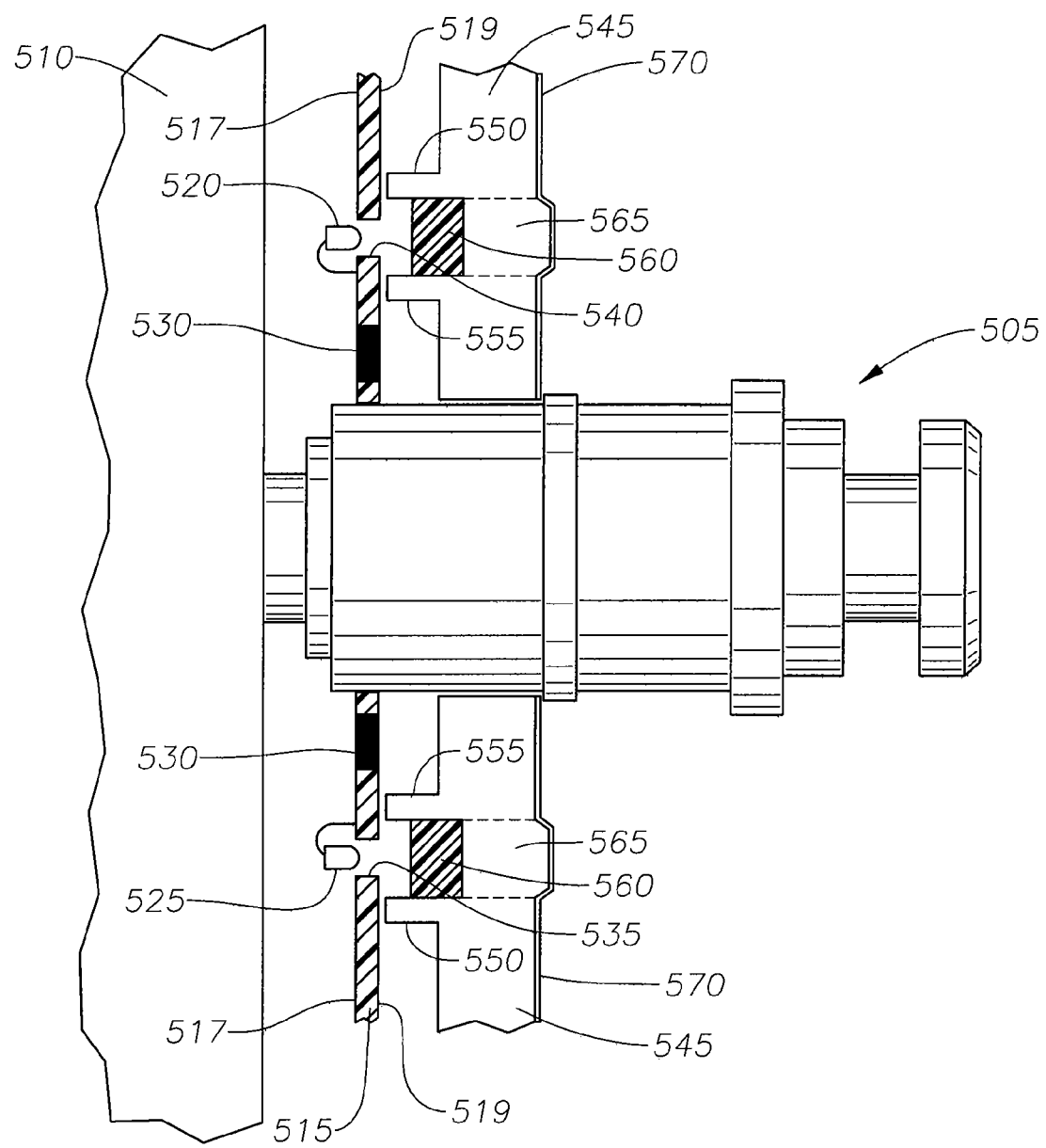
FIG. 5 is an exploded cross-section view of one implementation of an illumination ring on the front panel of a surgical machine according to an embodiment of the present invention.

FIG. 5 is an exploded cross-section view of one implementation of an RFID and illumination ring system according to an embodiment of the present invention. In FIG. 5, male connector 505 extends outward from the front of the surgical machine. Male connector 505 is connected to manifold 510. Manifold 510 is typically a metal housing that contains the internal circuitry of the surgical machine. Male connector 505 is generally cylindrical and is adapted to couple with a female connector of a surgical tool. When connected, male connector 505 provides power to the tool.

Front panel 545 forms the front skin of the surgical machine. Front panel 545 is typically made of a polymer such as PMMA, PC, PS, HDPE, Silicon, PVC, or other plastic material. Using a polycarbonate is preferable because it can be have a V-0 flame rating at a lesser thickness than that required for other types of plastics. For example, a GE LEXAN 9945A polycarbonate is a suitable choice for front panel 545. Front panel 545 includes two concentric circular ribs 550, 555. These ribs protrude outward from the inner surface of front panel 545 and toward manifold 510. These ribs 550, 555 establish the inner and outer diameter of circular prism array 560. Prism array 560 is in the shape of a ring that is concentrically disposed around male connector 505. Area 565 is a translucent portion of front panel 545 that allows light from LEDs 520, 525 to be visible from the front of front panel 545. In the configuration shown in FIG. 5, ribs 550, 555, prism array 560, and area 565 are all in the form of a ring that is disposed around male connector 505. Optional diffusive layer 570 is located on the outer surface of front panel 545.

PCB 515 is located between front panel 545 and manifold 510. PCB 515 has a circular hole through which male connector 505 extends. PCB 515 also has an RFID reader antenna 530. RFID reader antenna 530 is mounted on PCB 515 in a circular region around male connector 505. RFID antenna is preferably mounted on the front surface 519 of PCB 515, but may be incorporated into the PCB 515 itself. RFID reader antenna 530 can have any one of a number of different shapes or configurations. For example, RFID reader antenna 530 may be in the shape of a spiral.

PCB 515 also has LEDs 520, 525 mounted on its back surface 517. Openings 535, 540 allow light from LEDs 525, 520 to travel to prism array 560. In the exemplary embodiment show in FIG. 5, LEDs 520, 525 are mounted such that their light producing elements are disposed in openings 540, 535, respectively.

In operation, light from LED 520 passes through opening 540 and light from LED 525 passes through opening 535. This light travels to different sections of prism array 560. Prism array 560 is designed to refract and internally reflect the light emitted by LEDs 520, 525. In this manner, prism array 560 acts to scatter the light in a circular pattern and into area 565. Area 565, like prism array 560 is in the shape of a ring. The refracted light travels through area 565 where it may be diffused. Alternatively, the scattered light travels through area 565 to diffusive layer 570 where it is diffused.

In the configuration shown, area 565 can be either a transparent or a translucent plastic. If it is translucent, area 565 acts to diffuse the light that is refracted and/or internally reflected by prism array 560. If it is transparent, area 565 may simply transmit the light to diffusive layer 570. Diffusive layer 570 may then diffuse the light.

Diffusive layer 570 is optional. If it is not used, then area 565 and prism array 560 are designed to diffuse the light produced by LEDs 520, 525. In addition, a texture may be added to the outer surface of front panel 545. This texture (not shown) also operates to diffuse light. A texture may also be applied to diffusive layer 570. If present, diffusive layer 570 may be made of a mechanically anti-microbial polymer.

In either configuration, a ring of light is visible from the front panel 570 when LEDs 520, 525 are illuminated. These LEDs 520, 525 are illuminated when a female connector on a tool (not shown) comes into proximity with RFID reader antenna 530. In this manner, a tag contained on the female connector enters the field radiated from RFID reader antenna 530. The RFID reader antenna 530 receives a signal from the tag. In other words, the RFID reader reads the tag. The LEDs 520, 525 are illuminated in response to the information read from the tag.

The LEDs 520, 525 are preferably multicolor LEDs. To produce different colors, it is also possible to use different LEDs, each producing a different color light. In this manner, only the same color LEDs are illuminated at a given time to produce a particular color light. For example, red LEDs may be illuminated to produce a circular red light on the front panel 545 of the surgical machine. In another mode of operation, two different color LEDs can be illuminated to produce a third color. For example, a yellow and a blue LED may be illuminated to produce a green circular light on the front panel 545 of the surgical machine.

As shown in FIG. 5, both the RFID reader antenna 530 and the LEDs 525, 520 are located on the same PCB 515. This provides the advantage of having fewer parts to assemble in the manufacturing process. In addition, the PCB 515 is located close to front panel 545. It is desirable to locate RFID reader antenna 530 close to the front panel 545 so that it can more easily read information from an RFID tag that is brought close to it. In addition, placing the RFID reader antenna 530 close to front panel 545, allows the field radiated by RFID reader antenna 530 to extend further beyond front panel 545 thereby increasing the read and write distance of the RFID system.

However, since RFID reader antenna 530 is on the same PCB 515 as LEDs 520, 525, the LEDs 520, 525 are located close to the front panel 545. When the LEDs 520, 525 are located close to the front panel, it becomes more difficult to refract and diffuse the light produced by them into a concentric ring. In general, the closer a light source is to a prism array, the more difficult it is to refract and diffuse or scatter the light. Therefore, prism array 560 is designed to properly refract the light produced by LEDs 520, 525. Additionally, a polymer with proper diffusive characteristics, like a translucent polycarbonate, is chosen for front panel 545 and area 565.

Figure 6:
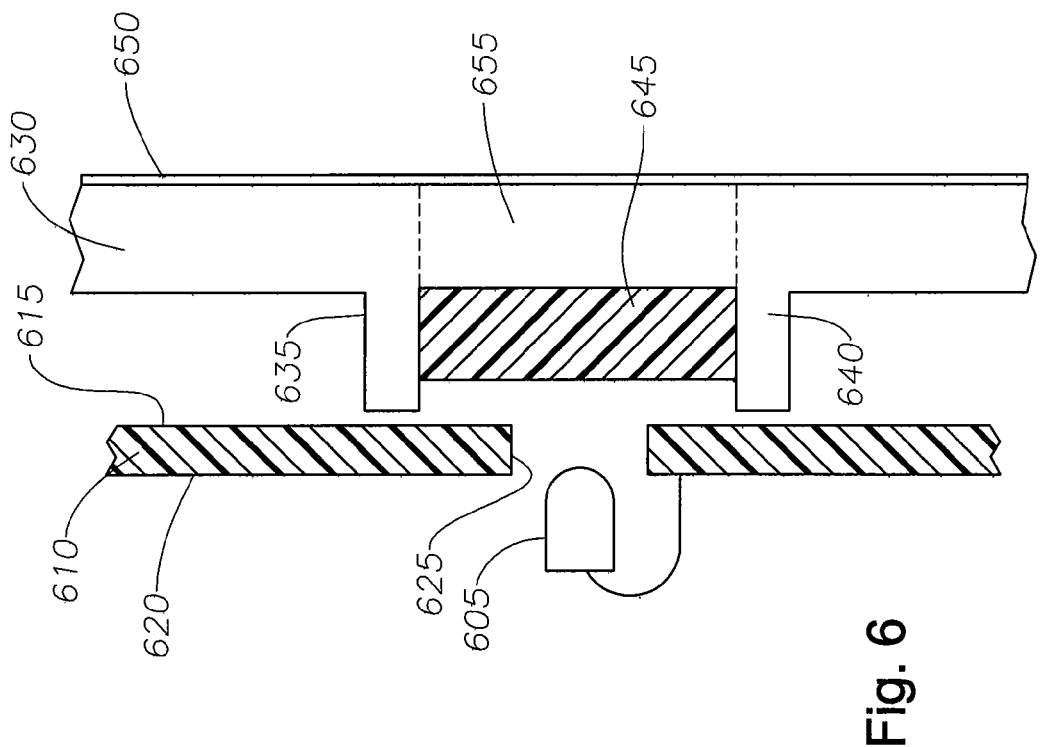
FIG. 6 is a detailed cross-section view of a module incorporating an RFID ring illumination system according to an embodiment of the present invention.

FIG. 6 is a detailed cross-section view of a module incorporating an RFID ring illumination system. In FIG. 6, the ring illumination system is implemented in a module that attaches to the front of a surgical machine instead of being implemented in the front panel or skin of the surgical machine. The module can be manufactured separately and then assembled onto the surgical machine.

In FIG. 6, the module includes a polymer structure 630 with ribs 635 and 640, area 655, and prism array 645. Optional diffusive layer 650 is located on the front surface of polymer structure 630. Ribs 635, 640 extend outward from the back of polymer structure 630. As in FIG. 5, ribs 635, 640 establish the boundaries for prism array 645. In this case, ribs 635, 640 are in the shape of concentric circles. Therefore, prism array 645 and area 655 are in the shape of rings that are stacked on top of each other. The module also includes a PCB 610 with LED 605 mounted on its back face 620. Opening 625 extends from back face of PCB 620 to front face 615. Front face of PCB 610 is adjacent to ribs 635, 640 and prism array 645.

The operation of the module of FIG. 6 is similar to that of the assembly of FIG. 5. In FIG. 6, light from LED 605 travels through opening 625 in PCB 610 to prism array 645. Prism array 645 refracts, internally reflects and possibly diffuses the light from LED 605. The refracted, internally reflected or scattered light then passes through area 655 where it also may be diffused. Optional diffusive layer 650 diffuses the light as it leaves the front of the module and travels to a person's eye. When viewed from the front of the module, a continuous ring of light is seen when LED 605 (and other LEDs not shown) are illuminated. The operation and variation of the different elements is the same as in similar components described with respect to FIG. 5. For example, the RFID reader antenna can be located on the PCB 610 in the same manner as disclosed with respect to FIG. 5.

Figure 7:
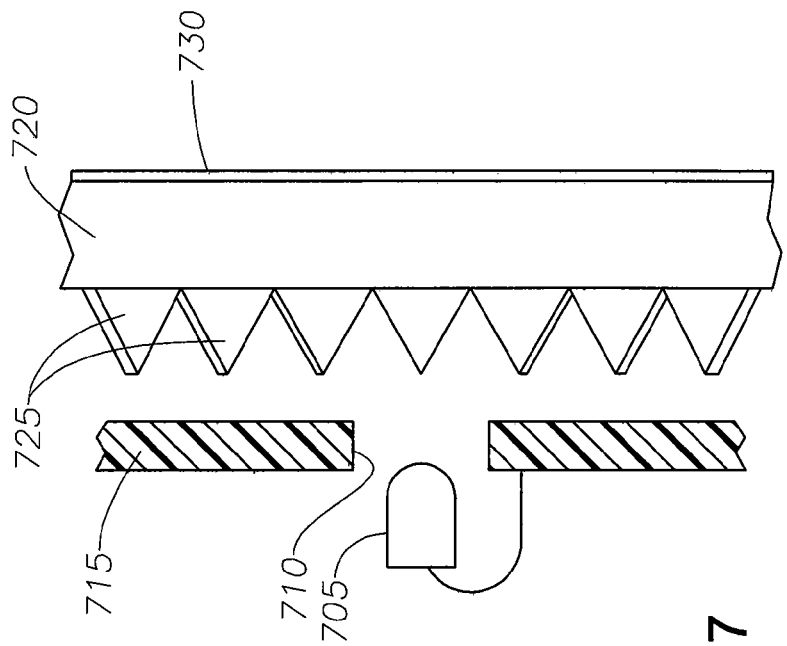
FIG. 7 is a more detailed view of FIG. 5 as seen from a different angle.

FIG. 7 is a more detailed view of FIG. 6 as seen from a different angle. In FIG. 7, the structure of the prism array 725 is more clearly shown. In this cross section of the module or front panel that implements an illumination ring, LED 705 is located on the back surface of PCB 715. PCB 715 has an opening 710 through which light can pass. Adjacent to PCB 715 is prism array 725. The prism array is integral with area 720 of the polymeric material used to form the illumination ring structure. Optional diffusive layer 730 is located on the outer surface of the front panel or module. Prism array 725 has triangular teeth arranged in a circle. Prism array 725 need not have symmetrical triangular shaped teeth. The teeth could be skewed triangles, sinusoids, or any combination thereof.

Figure 8:
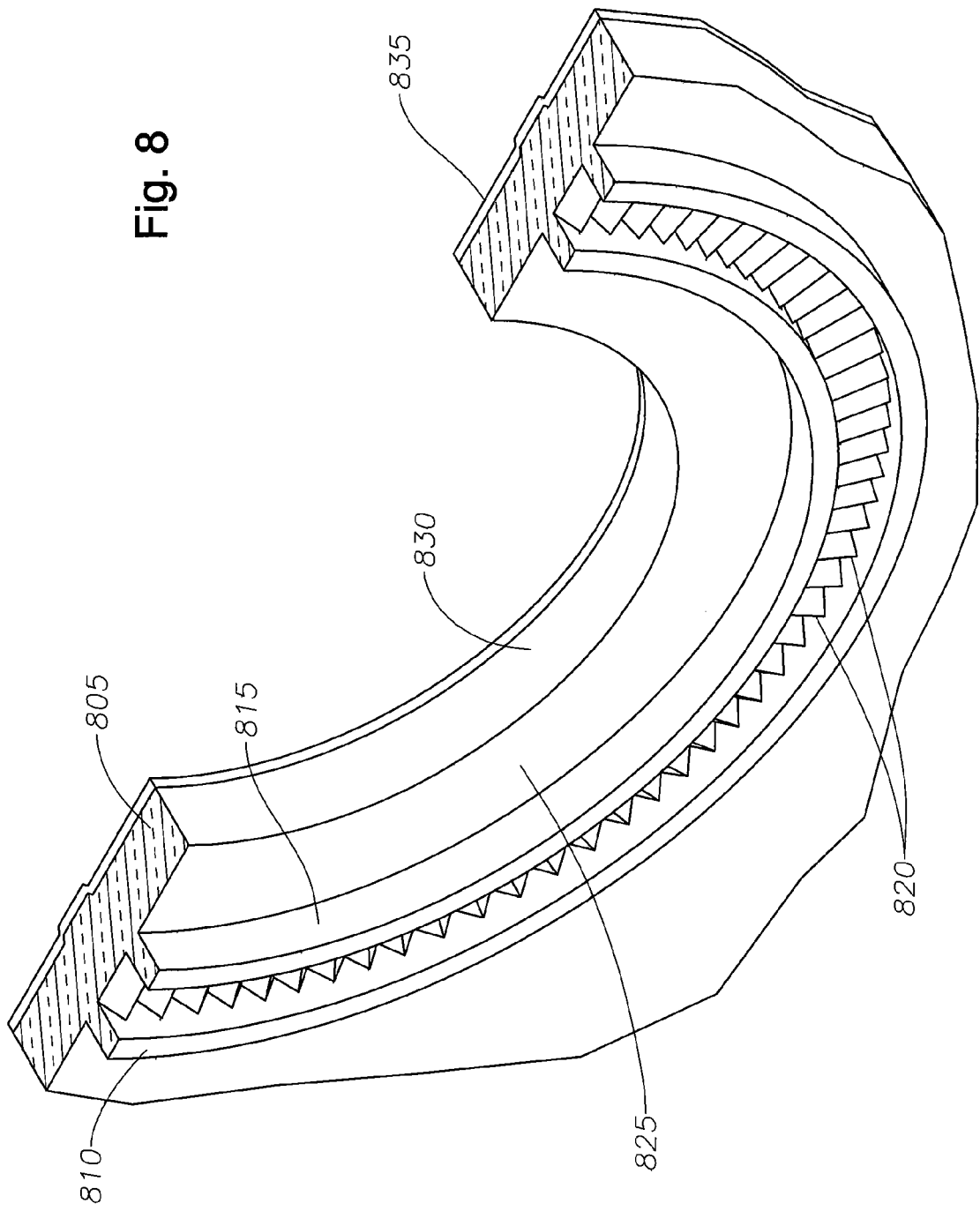
FIG. 8 is a cross-section perspective view of one implementation of an illumination ring integral to front panel of a surgical machine according to an embodiment of the present invention.

The configuration of the prism array is more easily seen in FIG. 8. FIG. 8 is a cross-section perspective view of one implementation of an illumination ring. Prism array 820 consists of triangular teeth arranged in a circle. Alternatively, the prisms could be sinusoidal or in the shape of skewed triangles. Ribs 810, 820 establish the boundaries of prism array 820. Prism array 820 and ribs 810, 815 are integral with polymer structure 805. Optional diffusive layer 835 is located on an outer surface of polymer structure 805. Circular surface 830 forms an opening through which male connector 505 protrudes.

Figure 9:
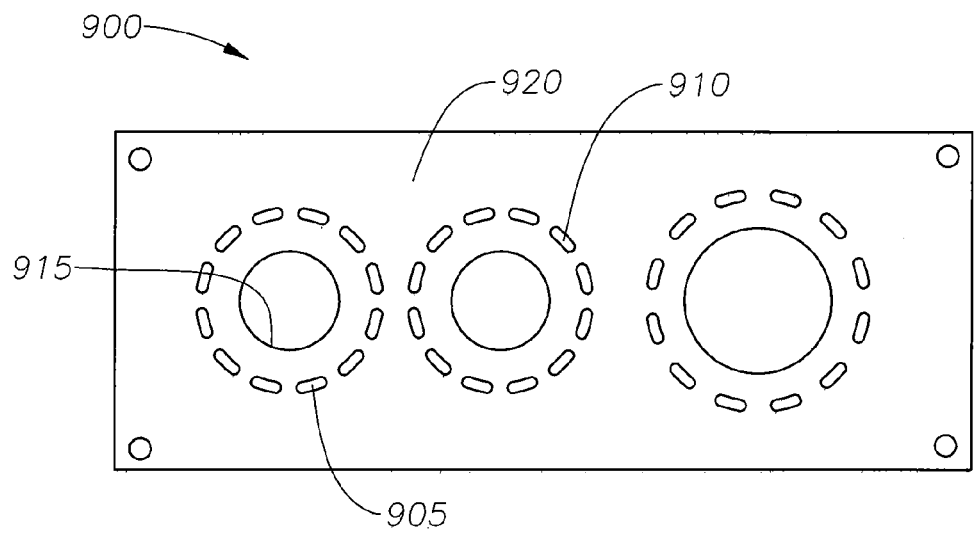
FIG. 9 is a perspective view of a printed circuit board according to an embodiment of the present invention.

FIG. 9 is a perspective view of a printed circuit board according to an embodiment of the present invention. PCB 900 has openings for three connectors. Connector opening 915 is designed to allow a male connector 505 to pass through PCB 900 and attach to manifold 510. LED openings 905, 910 are designed to allow light to pass through the PCB 900. LEDs (not shown) are mounted on the back surface 920 of PCB 900. The light produced by the LEDs travels through LED openings 905, 910. While shown as a kidney shape, LED openings 905, 910 may be any shape that allows light to pass through PCB 900. In FIG. 9, each LED (not shown) has its own LED opening 905, 910 associated with it. An LED is mounted on the back surface 920 of PCB 900 adjacent to LED opening 905. The LED may also be mounted on the back surface 920 of PCB 900 such that the LED protrudes through LED opening 905. In this manner, the leads of LED 905 are mounted on the back surface 920 of PCB 900, but the light producing part of the LED extends over the LED opening 905.

In FIG. 9, each illumination ring is implemented with 12 LEDs. There are also 12 LED openings. In practice, any number of LEDs can be used. The number used depends on the diameter of the illumination ring, the type of LEDs used, and the desired quality of light to be viewed from the front of the surgical machine.

Figure 10:
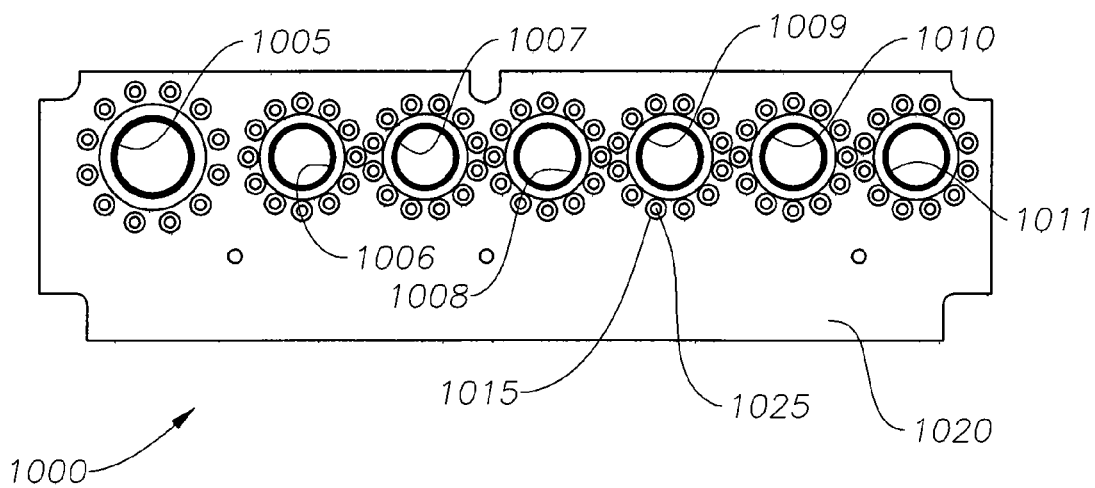
FIG. 10 is a view of a printed circuit board with LEDs according to an embodiment of the present invention.

FIG. 10 is a perspective view of a printed circuit board with LEDs according to an embodiment of the present invention. PCB 1000 has openings for seven connectors. Connector openings 1005, 1006, 1007, 1008, 1009, 1010, 1011 are each designed to allow a male connector 505 to pass through PCB 1000 and attach to manifold 510. Each connector opening 1005, 1006, 1007, 1008, 1009, 1010, 1011 has 12 LED openings, such as LED opening 1015, associated with it. The LED openings, such as LED opening 1015, is designed to allow light to pass through the PCB 1000. LEDs, such as LED 1025 is mounted on the back surface 1020 of PCB 1000. The light produced by the LEDs, such as LED 1025, travels through the LED openings, such as LED opening 1015. While shown as an oval, LED openings, such as LED opening 1015, may be any shape that allows light to pass through PCB 1000. In FIG. 10, each LED (shown as a rectangle) has its own LED opening associated with it. An LED is mounted on the back surface 1020 of PCB 1000 adjacent to an LED opening. The LED may also be mounted on the back surface 1020 of PCB 1000 such that the LED protrudes through the LED opening. In this manner, the leads of LED 1025, for example, are mounted on the back surface 1020 of PCB 1000, but the light producing part of the LED 1025 extends over the LED opening 1015. In FIG. 10, each LED (shown as a rectangle) is disposed over an LED opening (shown as an oval).

In FIG. 10, each illumination ring is implemented with 12 LEDs. There are also 12 LED openings. In practice, any number of LEDs can be used. The number used depends on the diameter of the illumination ring, the type of LEDs used, and the desired quality of light to be viewed from the front of the surgical machine.

FIGS. 11-14 are perspective views of the front and back of molded plastic parts that fit onto a surgical machine. Each of these molded plastic parts implements a set of illumination rings. A PCB with LEDs (not shown), such as the PCBs depicted in FIGS. 9 and 10, is placed adjacent to the back of each of the molded plastic parts. The molded plastic parts of FIGS. 11-15 each contain prism arrays and various layers of plastics as described above.

Figure 11:
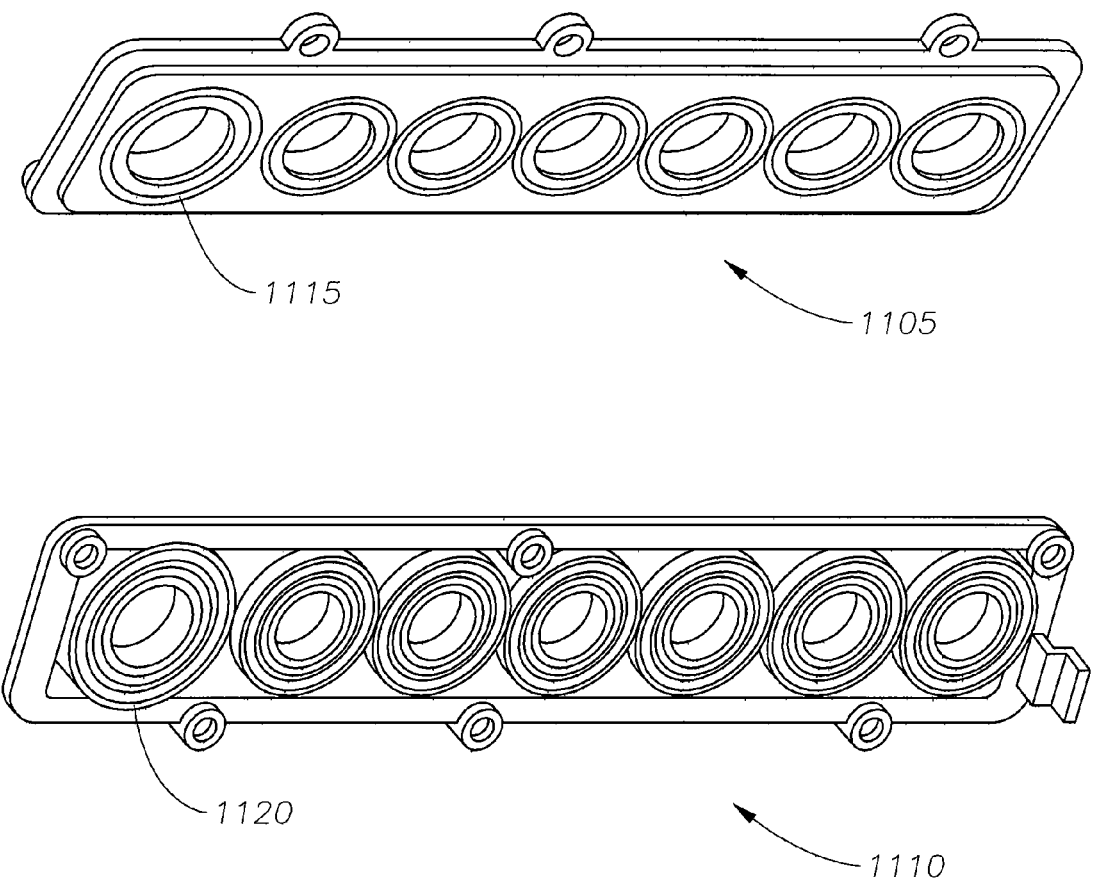
FIG. 11 is a perspective view of one embodiment of an RFID ring illumination system located on a surgical machine.

In FIG. 11, a front view 1105 and a back view 1110 of a molded plastic panel is shown. This molded plastic panel is configured to attach to and form the front skin of a surgical machine. There are seven illumination rings shown on this panel. The front 1115 and back 1120 of one illumination ring is depicted.

Figure 12:
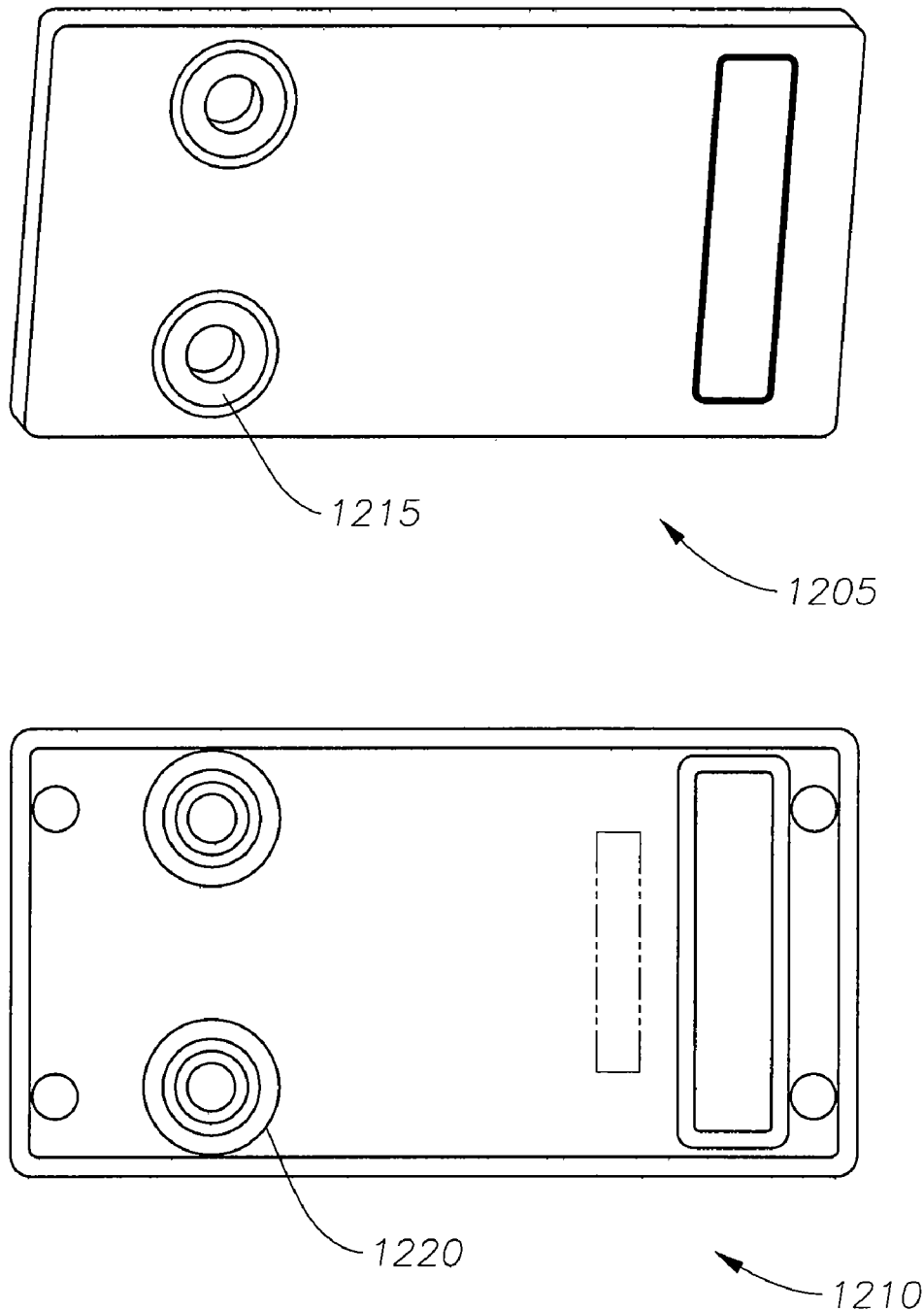
FIG. 12 is a perspective view of one embodiment of an RFID ring illumination system located on a surgical machine.

In FIG. 12 a front view 1205 and a back view 1210 of a molded plastic panel is shown. This molded plastic panel is configured to attach to and form the front skin of a surgical machine. There are two illumination rings shown on this panel. The front 1215 and back 1220 of one illumination ring is depicted.

Figure 13:
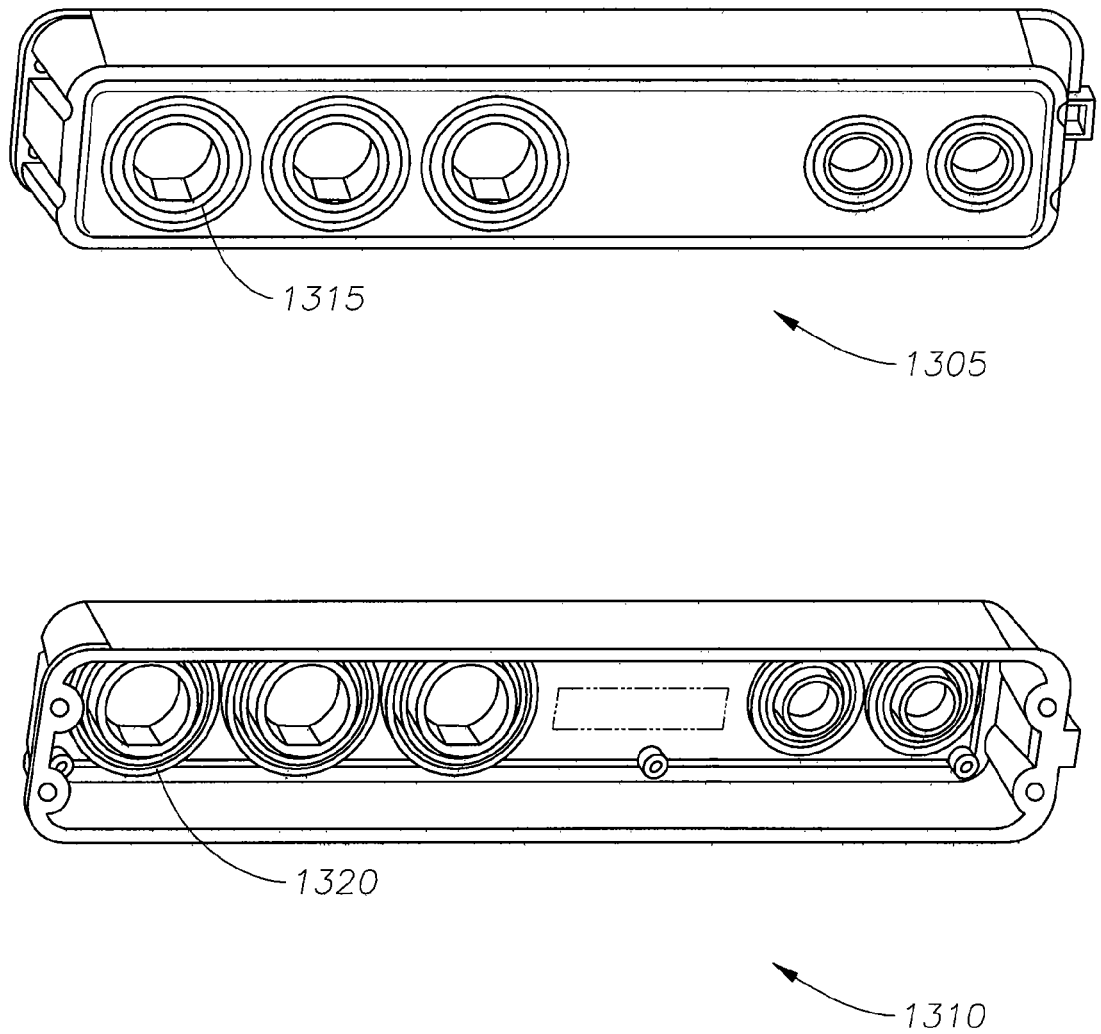
FIG. 13 is a perspective view of one embodiment of an RFID ring illumination system located on a surgical machine.

In FIG. 13, a front view 1305 and a back view 1310 of a molded plastic panel is shown. This molded plastic panel is configured to attach to and form the front skin of a surgical machine. There are five illumination rings shown on this panel. The front 1315 and back 1320 of one illumination ring is depicted.

Figure 14:
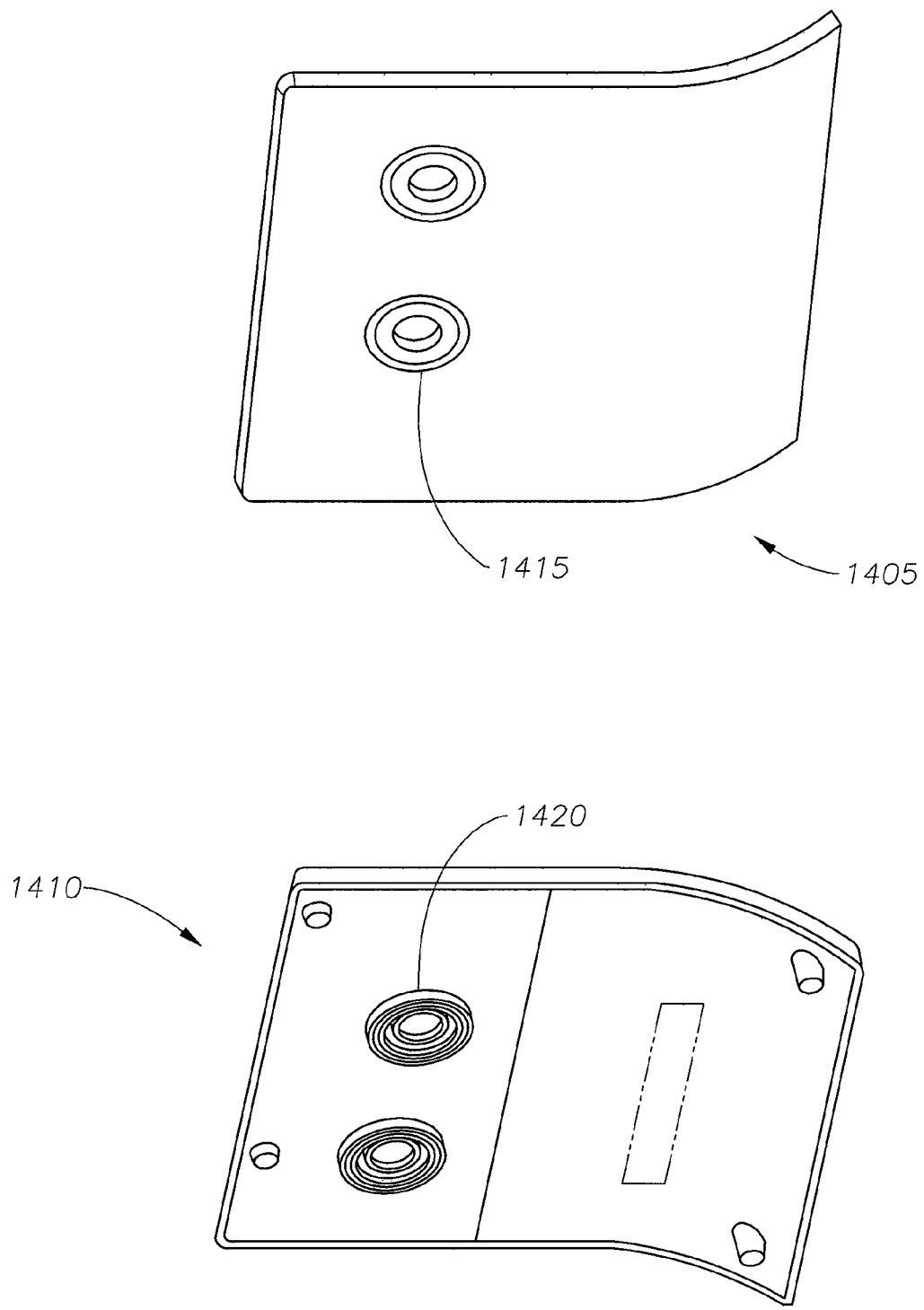
FIG. 14 is a perspective view of one embodiment of an RFID ring illumination system located on a surgical machine.

In FIG. 14, a front view 1405 and a back view 1410 of a molded plastic panel is shown. This molded plastic panel is configured to attach to and form the front skin of a surgical machine. There are two illumination rings shown on this panel. The front 1115 and back 1120 of one illumination ring is depicted.

In one specific example, the prism facets have a 0.04 inch pitch (inter-prism spacing). The base of the prisms are located 0.06 inches from the LED. The LEDs are separated by a distance of 0.52 inches. The depth of the prisms is 0.03 inches. Uniform scaling can be applied to these parameters to produce larger or smaller illumination rings. The amount of diffusion can be adjusted by increasing or decreasing the amount of opacity in the base material used to form the illumination ring.

In general, there is a relationship between the opacity of the polymer used, the texture of the viewing surface, the angle of the prisms, the distance from the LEDs to the prisms, the thickness of the substrate, the brightness of the LEDs, the spacing of the LEDs, the size of the openings in the PCB, the location of the LEDs with respect to the opening, and the diameter of the ring.

The more opacity in the base material, the more light diffusion occurs. However, for more opaque materials, the LEDs need to be brighter to produce enough light to create an aesthetic ring of light. Alternatively, more LEDs could be used or they could be placed closer to the prisms. The openings could be made larger and the LEDs oriented in the openings to increase the amount of visible light.

In addition, brightness uniformity across the ring increases and peak ring brightness decreases as angular bandwidth of the LED increases. Brightness uniformity across the ring increases as inter-prism spacing decreases. However, if the prism array has prism edges that are not perfectly sharp but instead have a small radius of curvature, then as the inter-prism spacing decreases, the effects of the curved prism edges—essentially diffusion of light—become increasingly dominant. The potential brightness uniformity increases (and the peak brightness decreases) as distance between the LEDs and prism array increases. The brightness uniformity increases (and the peak brightness decreases) as the diffusion of the plastic increases. The brightness uniformity and peak brightness increase as the number of LEDs placed into the ring of fixed diameter increases.

From the above, it may be appreciated that the present invention provides an improved RFID illumination ring system for use on a surgical machine. The present invention helps the surgeon to connect the proper tool for use with a surgical machine. The structure of the illumination ring itself is also easier to manufacture and provides a surgical machine that is easier to keep clean. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A ring illumination system comprising:
   an illumination ring integral with a front of a surgical machine, the illumination ring comprising a light refracting layer; and
   a printed circuit board located behind and close to the front of the surgical machine, the printed circuit board comprising an RFID reader antenna and a light source; the printed circuit board further comprising a set of openings to allow light from the light source to reach the illumination ring;
   wherein light emitted by the light source travels through the illumination ring and is visible from the front of the surgical machine.

2. The system of claim 1 further comprising:
   a light diffusing layer disposed on the front of the surgical machine.

3. The system of claim 1 wherein the printed circuit board is located on a plane generally parallel with the front of the surgical machine.

4. The system of claim 1 wherein the face of the illumination ring exposed on the front of the surgical machine is textured.

5. The system of claim 1 wherein the light source is a set of light emitting diodes located on a face of the printed circuit board furthest from the front of the surgical machine.

6. The system of claim 1 wherein the RFID reader antenna is located on a face of the printed circuit board closest to the front of the surgical machine.

7. The system of claim 1 wherein the light refracting layer is a set of prisms.

8. A ring illumination system comprising:
   a module having a front face and a back face;
   an illumination ring integral with the module and extending from the front face of the module to the back face of the module; and
   a printed circuit board located behind and close to the back face of the module, the printed circuit board having an RFID reader antenna and a light source; the printed circuit board further comprising a set of openings to allow light from the light source to reach the back face of the module;
   wherein light emitted by the light source travels through the illumination ring and is visible from the front face of the module.

9. The system of claim 8 wherein the illumination ring comprises a set of prisms for refracting light emitted from the light source.

10. The system of claim 8 further comprising: a light diffusing layer disposed on the front face of module.

11. The system of claim 8 wherein the front face of the module is textured.

12. The system of claim 8 wherein the printed circuit board is located on a plane generally parallel with the front face of the module.

13. The system of claim 8 wherein the light source is a set of light emitting diodes located on a face of the printed circuit board furthest from the back face of the module.

14. The system of claim 8 wherein the RFID reader antenna is located on a face of the printed circuit board closest to the back face of the module.

15. The system of claim 8 wherein the illumination ring diffuses light from the light source.

16. The system of claim 8 wherein the light source is capable of producing at least two different colors of light.

17. A ring illumination system comprising:
a light diffusing layer integral with a front cover of a surgical machine;
a light refracting layer integral with the front cover of the surgical machine, the light refracting layer comprising a set of prisms arranged in a generally circular pattern; and
a printed circuit board located behind, close to, and generally parallel with the front cover of the surgical machine, the printed circuit board comprising an RFID reader antenna located on a face of the printed circuit board closest to the front cover of the surgical machine, the printed circuit board further comprising a set of light emitting diodes located on a face of the printed circuit board furthest from the front cover of the surgical machine, the printed circuit board further comprising a set of openings to allow light from the light emitting diodes to reach the light refracting layer;
wherein the light from the light emitting diodes is refracted by the light refracting layer and is diffused by the light diffusing layer to form a generally circular ring of light visible from the front cover of the surgical machine.

* * * * *